United States Patent
Irish et al.

(10) Patent No.: US 9,903,851 B2
(45) Date of Patent: Feb. 27, 2018

(54) THERMOELECTRIC POWERED WIRELESS VEHICLE SYSTEM SENSOR SYSTEMS

(71) Applicant: GM GLOBAL TECHNOLOGY OPERATIONS LLC, Detroit, MI (US)

(72) Inventors: Nicholas P. Irish, Milford, MI (US); James R. Salvador, Royal Oak, MI (US); William L. Villaire, Clarkston, MI (US)

(73) Assignee: GM Global Technology Operations LLC, Detroit, MI (US)

(*) Notice: Subject to any disclaimer, the term of this patent is extended or adjusted under 35 U.S.C. 154(b) by 260 days.

(21) Appl. No.: 14/812,039

(22) Filed: Jul. 29, 2015

(65) Prior Publication Data

US 2016/0031394 A1    Feb. 4, 2016

Related U.S. Application Data

(60) Provisional application No. 62/032,256, filed on Aug. 1, 2014.

(51) Int. Cl.

| | | |
|---|---|---|
| *H01L 35/30* | (2006.01) | |
| *G01N 33/28* | (2006.01) | |
| *H02J 7/00* | (2006.01) | |
| *H02J 7/02* | (2016.01) | |
| *G01F 23/14* | (2006.01) | |
| *F01N 5/02* | (2006.01) | |
| *G01F 23/00* | (2006.01) | |

(52) U.S. Cl.
CPC ......... *G01N 33/2852* (2013.01); *F01N 5/025* (2013.01); *G01F 23/0076* (2013.01); *G01F 23/14* (2013.01); *H01L 35/30* (2013.01); *H02J 7/0052* (2013.01); *H02J 7/0063* (2013.01); *H02J 7/025* (2013.01); *Y02T 10/16* (2013.01)

(58) Field of Classification Search
CPC ...... B60R 16/023; B60R 16/033; H01L 35/30
USPC ......................................................... 307/9.1
See application file for complete search history.

(56) References Cited

U.S. PATENT DOCUMENTS

| | | |
|---|---|---|
| 7,012,554 B2 | 3/2006 | Hiller et al. |
| 7,183,666 B2 | 2/2007 | Arakawa et al. |
| 2003/0062987 A1 | 4/2003 | Funayose |
| 2003/0095038 A1 | 5/2003 | Dix |
| 2010/0236595 A1* | 9/2010 | Bell .................. F01P 9/06 136/205 |
| 2011/0248846 A1 | 10/2011 | Belov |
| 2012/0239308 A1 | 9/2012 | Miller |
| 2013/0269421 A1* | 10/2013 | Tichborne ............. H04Q 9/00 73/53.01 |
| 2016/0007525 A1 | 1/2016 | Drew |

(Continued)

FOREIGN PATENT DOCUMENTS

| | | |
|---|---|---|
| DE | 102004005151 | 9/2005 |
| WO | 0055583 | 9/2000 |

OTHER PUBLICATIONS

Office Action dated Jan. 6, 2017 in U.S. Appl. No. 14/812,043.

*Primary Examiner* — Robert Deberadinis
(74) *Attorney, Agent, or Firm* — Cynthia R. Parks; Parks IP Law LLC

(57) ABSTRACT

A vehicle includes a thermal harvesting device that is positioned adjacent a heat-generating vehicle system. The thermal harvesting device generates electricity based on a temperature differential in order to power a sensor and a wireless transmitter.

21 Claims, 4 Drawing Sheets

(56) References Cited

U.S. PATENT DOCUMENTS

2016/0031394 A1     2/2016   Irish
2016/0037238 A1     2/2016   Salvador

* cited by examiner

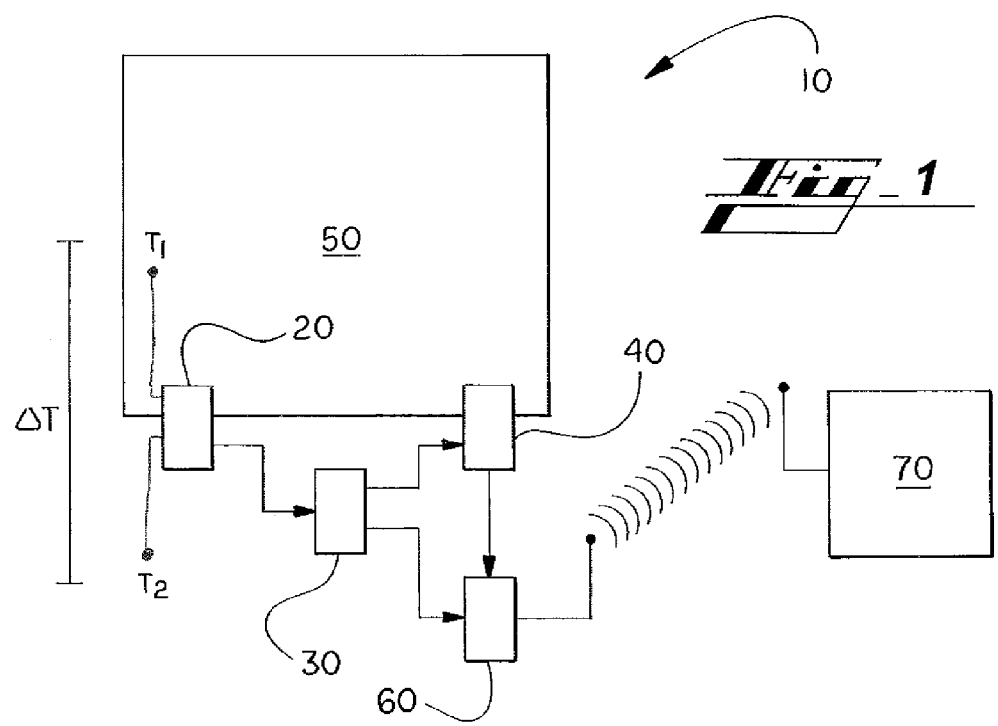
Fig_1
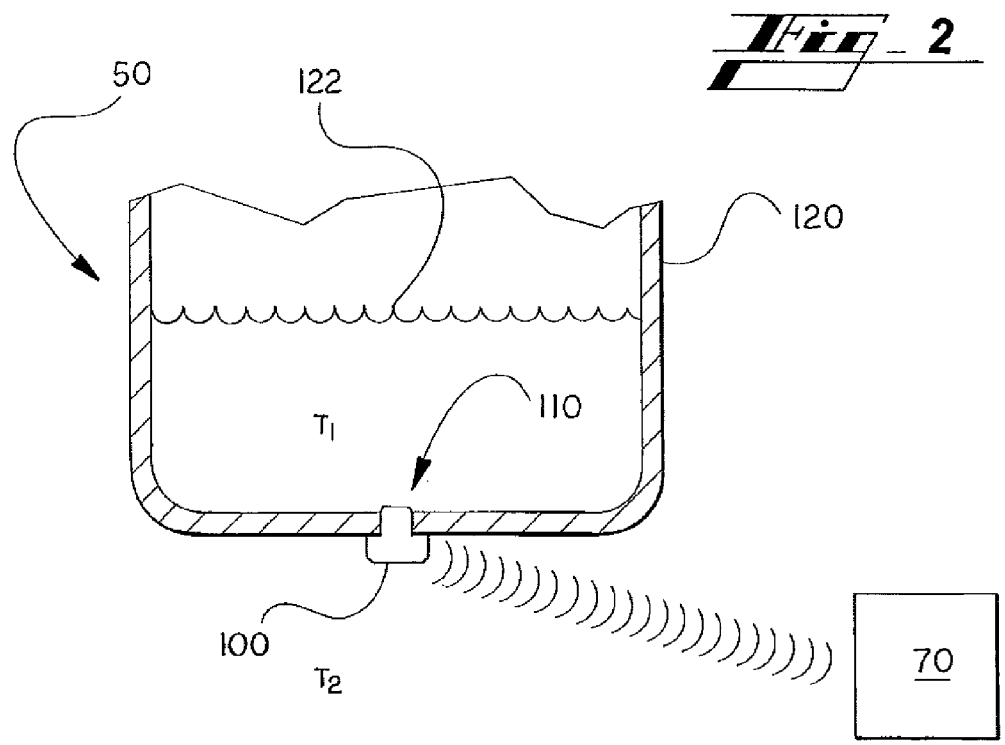
Fig_2

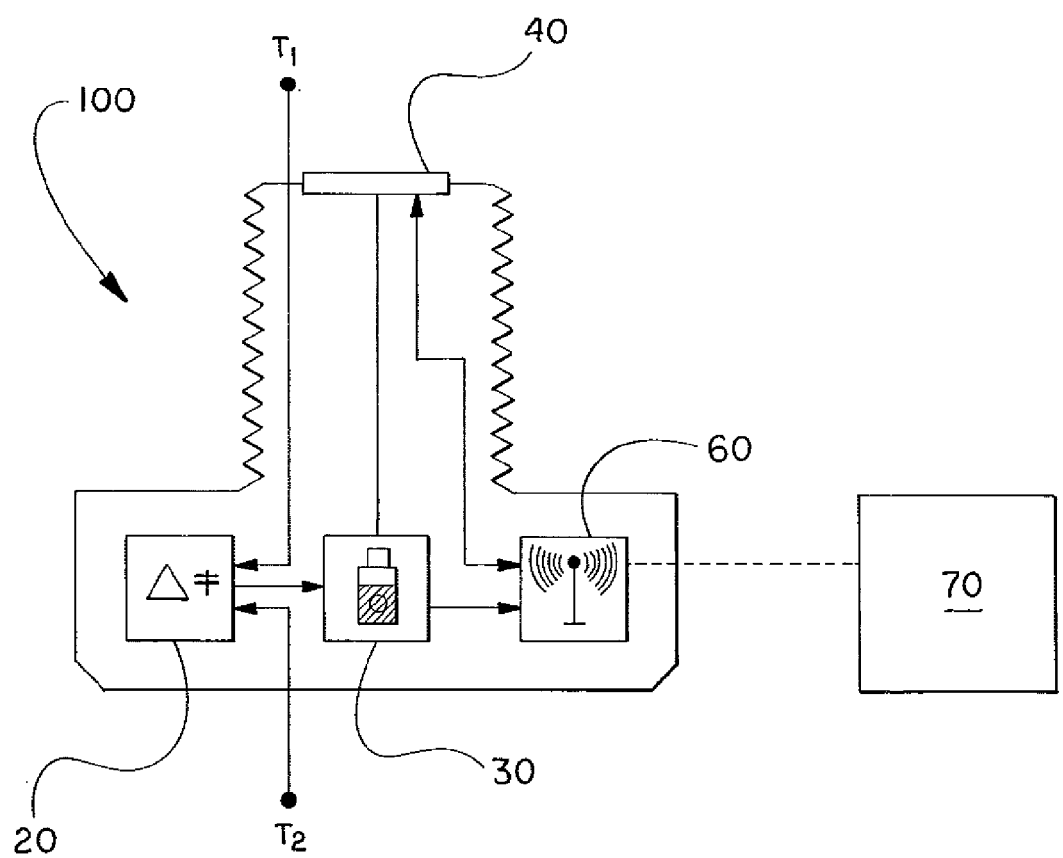
Fig_3

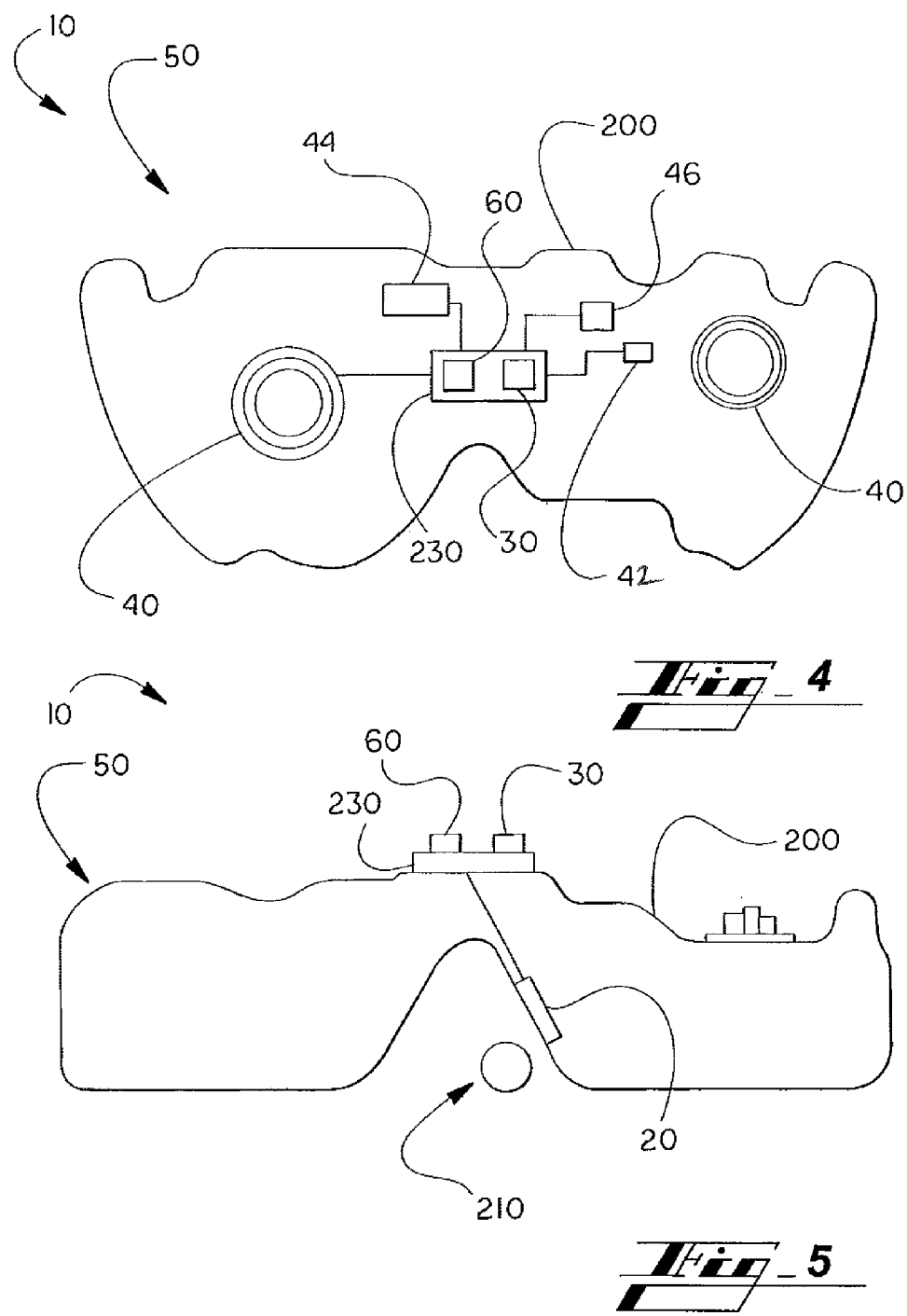

THERMOELECTRIC POWERED WIRELESS VEHICLE SYSTEM SENSOR SYSTEMS

TECHNICAL FIELD

The present disclosure relates generally to thermoelectric powered wireless vehicle system sensors.

BACKGROUND

Vehicle system sensors are powered by batteries, piezoelectric, or conventional twelve-volt direct current (DC). Batteries require periodic replacement. Piezoelectric harvesters have low energy density, have relatively low efficiency, durability, and reliability, and do not supply constant power. Conventional twelve-volt direct current (DC) has relatively high cost and weight due to the wires and wire harnesses in the chassis electrical system. The wires carry power to the various sensors and carry signals from the various sensors.

SUMMARY

The present technology relates to thermoelectric powered wireless vehicle system sensors. This disclosure describes a thermoelectric generator (TEG) (e.g., a thermoelectric module (TEM)) that provides power to both sensors and a wireless transmitter.

This technology reduces or eliminates transduction wires and harnesses; reduces wiring complexity; reduces power consumption by utilizing waste heat; increases manufacturability; reduces production costs; eliminates battery replacement; reduces battery cost (e.g., downsized rechargeable battery); increases efficiency, durability, and reliability (e.g., relative to piezoelectric); provides a reliable power source (e.g., dependent on duty cycle); and helps reduce mass. In addition, fewer electrical connections results in fewer failed connectors.

DESCRIPTION OF THE DRAWINGS

FIG. 1 illustrates schematically a vehicle, according to an embodiment of the present disclosure.

FIG. 2 illustrates schematically an oil storage system of the vehicle of FIG. 1.

FIG. 3 illustrates schematically a drain plug of the oil storage system of FIG. 2.

FIG. 4 illustrates schematically a plan view of a fuel storage system of the vehicle of FIG. 1.

FIG. 5 illustrates schematically a front view of the fuel storage system of FIG. 4.

Figure 6:
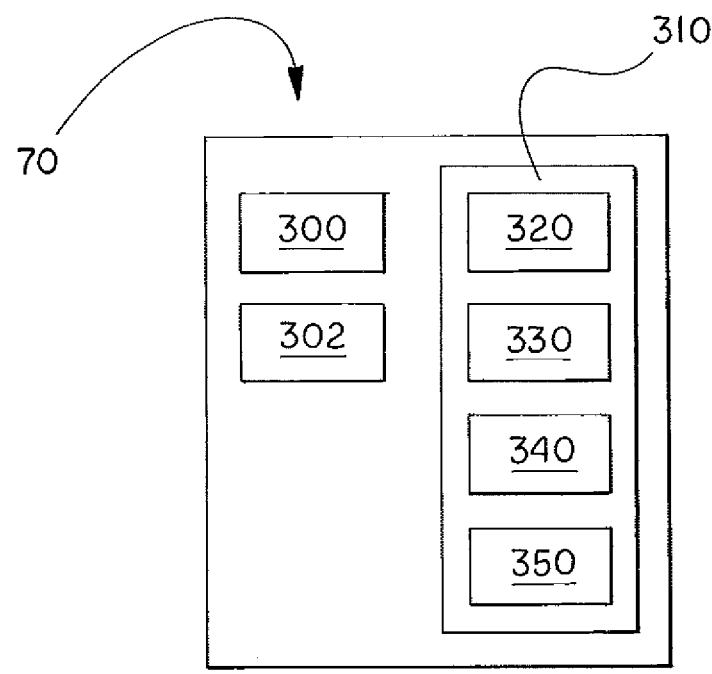
FIG. 6 illustrates a vehicle control unit of the vehicle of FIG. 1.

The figures are not necessarily to scale and some features may be exaggerated or minimized, such as to show details of particular components. In some instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to variously employ the present disclosure.

DETAILED DESCRIPTION

As required, detailed embodiments of the present disclosure are disclosed herein. The disclosed embodiments are merely examples that may be embodied in various and alternative forms, and combinations thereof. As used herein, for example, "exemplary," and similar terms, refer expansively to embodiments that serve as an illustration, specimen, model or pattern.

As used herein, the term "vehicle" is not limited to automobiles. While the present technology is described primarily herein in connection with automobiles, the technology is not limited to automobiles. The concepts can be used in a wide variety of applications, such as in connection with aircraft, marine craft, and other vehicles.

Vehicle

According to an embodiment illustrated in FIG. 1, a vehicle 10 includes a thermal harvesting device 20, a battery 30, a sensor 40 associated with a vehicle system 50, a wireless transmitter 60, and a computing unit 70.

The thermal harvesting device 20 is configured to generate electricity based on a temperature differential. The generated electricity powers the battery 30, powers another energy storage device such as a capacitor, or directly powers the sensor 40 and the wireless transmitter 60. As described in further detail below, the thermal harvesting device 20 is positioned at a location that generates heat or where there is a high temperature differential. For example, the vehicle system 50 generates heat and the location is on or adjacent to the vehicle system 50.

According to an exemplary embodiment, the sensor 40 is configured to be powered by the battery 30, to measure one or more characteristics reflecting a parameter of a vehicle system 50, and to output a signal including data corresponding to the measured characteristic (or, "measured data") to the wireless transmitter 60. The wireless transmitter 60 configured to be powered by the battery 30, to receive a signal from the sensor 40, and to wirelessly transmit the signal to the computing unit 70.

Thermal Harvesting Device

The thermal harvesting device 20 is configured to generate electricity based on a temperature differential. According to an exemplary embodiment, the thermal harvesting device 20 is a thermoelectric generator (TEG) or a thermoelectric module (TEM). A TEM is a device that converts heat (temperature differentials) directly into electrical energy, for example, using a phenomenon called the Seebeck effect.

Oil Storage System

Referring to FIGS. 2 and 3, the vehicle system 50 is an oil storage system and the sensor 40 measures one or more characteristics reflecting a parameter of the oil storage system 50. Sensors 40 of an oil storage system include those that measure the characteristic(s) reflecting any of oil level, oil quality, and oil properties including viscosity, aeration, and the like.

Referring to FIG. 3, the oil level sensor 40, the wireless transmitter 60, the battery 30, and the TEM 20 are housed in a drain plug 100. Referring to FIG. 2, the drain plug 100 is configured to be received in a threaded opening 110 in an engine oil pan 120. The engine oil pan 120 includes engine oil 122. For example, the oil level sensor 40 is a pressure sensor and a pressure measurement from the pressure sensor is provided to the control unit 70, which converts the pressure measurement into a value representing the oil level of the engine oil 122.

The TEM 20 is mounted in the drain plug 100 so as to be positioned at a location on the oil storage system 50 where there is a high temperature differential ($\Delta T$). Particularly, there is a temperature differential ($\Delta T$) between an engine oil temperature ($T_1$) (e.g., waste heat) and the ambient temperature ($T_2$) outside the engine oil pan 120. The temperature differential ($\Delta T$) is across the TEM 20 and causes the TEM 20 to output power (i.e., to harvest the waste heat).

The power from the TEM 20 charges the rechargeable battery 30 (or batteries) and maintains the state of charge of the battery 30. Because the battery 30 is trickle charged by the TEM 20, the battery 30 does not need to be replaced or serviced. In certain embodiments, a capacitor is substituted for the battery. In certain embodiments, the TEM 20 directly powers the oil level sensor 40 and the wireless transmitter 60.

The battery 30 provides a low power source to the oil level sensor 40 as well as to the wireless transmitter 60. Generally, a single TEM 20 can supply a battery with the power necessary to meet voltage and power requirements for operating a sensor and a wireless transmitter. For example, the power requirement of an exemplary oil level sensor is less than 23 milliWatts (mW) (power requirements will likely decrease in the near term) and the power requirement of a wireless transmitter is 15-200 microWatt ($\mu$W) depending on power-down current and bit transfer rates.

The wireless transmitter 60 receives a signal from the oil level sensor 40 and transmits the signal to the vehicle control unit 70. For example, the vehicle control unit 70 is a tire pressure monitoring system (TPMS).

The TEM 20 is sealed in epoxy or a protective material to prevent contamination with oil. Oil, debris and particulates in the oil, and environmental contaminants such as water, salt, and dirt can lead to shorts in the TEM and loss of power.

After the engine is off, the battery 30 continues to power the oil level sensor 40 and wireless transmitter 60. The oil level sensor 40 takes measurements at larger time intervals (e.g., at 5 hour intervals) such that the power supplied by the battery 30 is relatively small.

One advantage of the oil level sensor 40 is that accurate and real time oil level sensing removes the need for a dip stick and the associated cost and packaging complexity.

Fuel Storage System

Referring to FIGS. 4 and 5, the vehicle system 50 is a fuel storage system. The fuel storage system 50 includes a fuel tank assembly 200 and a vehicle exhaust system 210.

Each of a plurality of sensors measure one or more characteristic reflecting a parameter of the fuel storage system 50. The sensors of the fuel storage system 50 include those that measure the characteristic(s) reflecting any of fuel level, liquid pressure, vapor pressure, ethanol, and the like. Here, the sensors include a fuel level sensor 40, a liquid pressure sensor 42, a vapor pressure sensor 44, and an ethanol sensor 46.

The TEM 20 is mounted on or near the fuel tank assembly 200 in close proximity to the vehicle exhaust system 210. The heat from the vehicle exhaust system 210 creates a temperature differential ($\Delta T$) across the TEM 20. The temperature differential ($\Delta T$) causes the TEM 20 to output power. The TEM 20 is sealed in epoxy or a similar material to protect it from environmental contaminants such as water, road salt, and dirt.

The power from the TEM 20 charges the rechargeable battery 30 (or batteries; capacitors; or directly powers the sensors 40, 42, 44, 46 and the wireless transmitter 60).

According to an exemplary embodiment, a sensor control unit 230 includes the battery 30, the wireless transmitter 60, and elements (e.g., such as those described below with respect to the control unit 70) such as a processor, memory, and applications.

The battery 30 of the sensor control unit 230 provides a low power source to the fuel level sensor 40, the liquid pressure sensor 42, the vapor pressure sensor 44, the ethanol sensor 46, and the wireless transmitter 60.

The sensor control unit 230 is configured to receive a signal from each of the fuel level sensor 40, the liquid pressure sensor 42, the vapor pressure sensor 44, and the ethanol sensor 46. The sensor control unit 230 is also configured, using the wireless transmitter 60, to transmit the signals to the control unit 70. For example, the vehicle control unit 70 is an engine control module (ECM) or a body control module (BCM).

Vehicle System

Other vehicle systems 50 include, for example, any of a heating-ventilation and air-conditioning system (HVAC), an air conditioning system, a braking system, an acceleration system, an entertainment or infotainment system (e.g., a radio and/or video playing system), a navigation system, a mirrors system (e.g., mirror adjustment systems), a seat system (e.g., seat adjustment systems), a window-control system, a door system (e.g., door lock control systems), a collision-avoidance systems a traction-control system, a horn system, a windshield-wiper system, a belt and/or hose system, an emission system, an engine, engine-cooling system, an exhaust system, a lighting system, a wiper system, a vehicle-starting system, a charging system, a batteries system, a steering system, a suspension system, transmission system, a switch system, a camera system, communication devices (e.g., OnStar devices and other wireless communication devices), systems that connect to auxiliary devices (e.g., Bluetooth devices, cellular phones), a cluster system, a center stack system, a heads-up display (HUD) system, a speech system, a gesture system, a sound system, and the like.

Sensors

The sensors 40 measure phenomena or characteristics and generate output data indicative of the measured characteristics. Measured phenomena or characteristics include system characteristics of the vehicle systems and environmental characteristics from an environment (inside or outside) of the vehicle 10. Environmental characteristics (e.g., sound in the vehicle, distance to objects around the vehicle) reflect the environment associated with the vehicle 10 and vehicle system characteristics reflect the status or performance of the vehicle systems 50.

For example, environmental sensors can include temperature sensors, traffic sensors, road type (e.g., highway, urban) sensors, weather (e.g., rain) sensors, occupancy sensors, cameras that measure distance to an object, a microphone, and the like.

For example, vehicle system sensors can include a gas tank level sensor, speed sensors, sensors associated with the vehicle systems described above, and the like.

As provided, the sensors can measure any of a wide variety of phenomena or characteristics. Sensors can measure, as further example, ignition position or states of the vehicle, whether the vehicle is being turned off or on, whether or to what degree the vehicle is within a distance of a location, a type of weather (e.g., rain), a level of weather (e.g., amount of rain), an outside temperature, an outside humidity, an outside wind temperature, a cabin temperature, a vehicle speed, occupancy of a seat in the vehicle, weight of an occupant of a seat in the vehicle (e.g., to identify occupancy and distinguish between a child and adult), who is in the cabin (e.g., as identified by the presence of auxiliary devices that are specific to a user), vehicle state (e.g., amount of gas in the tank, cabin temperature, amount of oil), driver state (e.g., how long the driver has been driving and how they are driving (e.g., erratically)), general conditions (e.g., weather, temperature, day, time), driving conditions (e.g., road type, traffic), and the like.

Vehicle Control Unit

The vehicle control unit 70 includes various electronic control units (ECU). The ECU is an embedded system that controls one or more electrical systems or subsystems in the vehicle 10. For example, ECUs include an electronic/engine control module (ECM), a powertrain control module (PCM), a transmission control module (TCM), a brake control module (BCM or EBCM), a central control module (CCM), a central timing module (CTM), a general electronic module (GEM), a body control module (BCM), a suspension control module (SCM), a control unit, and a control module. In certain embodiments, the vehicle control unit 70 includes a plurality of the individual control modules.

The vehicle control unit 70 is configured to receive or access the signals transmitted by the wireless transmitter 60.

Referring to FIG. 6, the vehicle control unit 70 includes a processor 300 for controlling and/or processing data, input/output data ports 302, and a memory 310.

The processor could be multiple processors, which could include distributed processors or parallel processors in a single machine or multiple machines. The processor could include virtual processor(s). The processor could include a state machine, application specific integrated circuit (ASIC), programmable gate array (PGA) including a Field PGA, or state machine. When a processor executes instructions to perform "operations," this could include the processor performing the operations directly and/or facilitating, directing, or cooperating with another device or component to perform the operations.

The vehicle control unit 70 can include a variety of computer-readable media, including volatile media, non-volatile media, removable media, and non-removable media. The term "computer-readable media" and variants thereof, as used in the specification and claims, includes storage media. Storage media includes volatile and/or non-volatile, removable and/or non-removable media, such as, for example, RAM, ROM, EEPROM, flash memory or other memory technology, CDROM, DVD, or other optical disk storage, magnetic tape, magnetic disk storage, or other magnetic storage devices or any other medium that is configured to be used to store information that can be accessed by the vehicle control unit 70.

While the memory 310 is illustrated as residing proximate the processor 300, it should be understood that at least a portion of the memory can be a remotely accessed storage system, for example, a server on a communication network, a remote hard disk drive, a removable storage medium, combinations thereof, and the like. Thus, any of the data, applications, and/or software described below can be stored within the memory and/or accessed via network connections to other data processing systems (not shown) that may include a local area network (LAN), a metropolitan area network (MAN), or a wide area network (WAN), for example.

The memory 310 includes several categories of software and data used in the vehicle control unit 70, including applications 320, a database 330, an operating system 340, and input/output device drivers 350.

As will be appreciated by those skilled in the art, the operating system 340 may be any operating system for use with a data processing system. The input/output device drivers 350 may include various routines accessed through the operating system 340 by the applications to communicate with devices, and certain memory components. The applications 320 can be stored in the memory 310 and/or in a firmware (not shown) as executable instructions, and can be executed by the processor 300.

The applications 320 include various programs that, when executed by the processor 300, implement the various features of the vehicle control unit 70. The applications 320 include control signal applications 320. The applications 320 are stored in the memory 310 and are configured to be executed by the processor 300.

The applications 320 may use data stored in the database 330, such as that of characteristics measured by the sensors 40 (e.g., received via the input/output data ports 302). The database 330 includes static and/or dynamic data used by the applications 320, the operating system 340, the input/output device drivers 350 and other software programs that may reside in the memory 310.

The control signal application 320 is configured to generate a control signal to control a vehicle system 50 based on characteristics measured by the sensors 40.

It should be understood that FIG. 6 and the description above are intended to provide a brief, general description of a suitable environment in which the various aspects of some embodiments of the present disclosure can be implemented. The terminology "computer-readable media", "computer-readable storage device", and variants thereof, as used in the specification and claims, can include storage media. Storage media can include volatile and/or non-volatile, removable and/or non-removable media, such as, for example, RAM, ROM, EEPROM, flash memory or other memory technology, CDROM, DVD, or other optical disk storage, magnetic tape, magnetic disk storage, or other magnetic storage devices or any other medium, excluding propagating signals, that can be used to store information that can be accessed by the device shown in FIG. 6.

While the description refers to computer-readable instructions, embodiments of the present disclosure also can be implemented in combination with other program modules and/or as a combination of hardware and software in addition to, or instead of, computer readable instructions.

While the description includes a general context of computer-executable instructions, the present disclosure can also be implemented in combination with other program modules and/or as a combination of hardware and software. The term "application," or variants thereof, is used expansively herein to include routines, program modules, programs, components, data structures, algorithms, and the like. Applications can be implemented on various system configurations, including single-processor or multiprocessor systems, minicomputers, mainframe computers, personal computers, hand-held computing devices, microprocessor-based, programmable consumer electronics, combinations thereof, and the like.

Method

Figure 7:
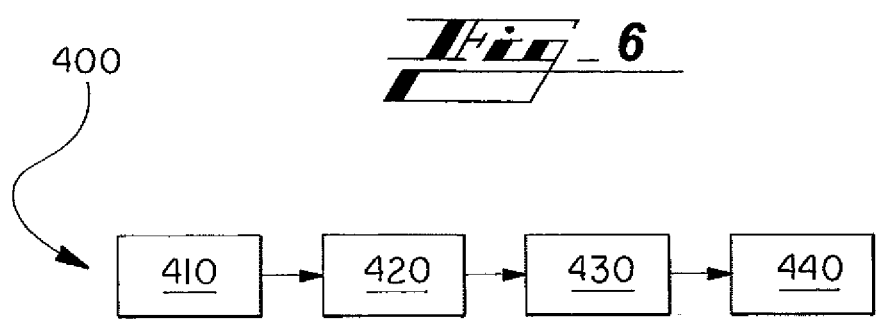
FIG. 7 illustrates an exemplary method of the vehicle of FIG. 1.

FIG. 7 shows a method 400 according to an embodiment of the present disclosure. It should be understood that the steps of methods are not necessarily presented in any particular order and that performance of some or all the steps in an alternative order is possible and is contemplated. The steps have been presented in the demonstrated order for ease of description and illustration. Steps can be added, omitted and/or performed simultaneously without departing from the scope of the appended claims.

It should also be understood that the illustrated methods can be ended at any time. In certain embodiments, some or all steps of this process, and/or substantially equivalent steps are performed by execution of computer-readable instructions (e.g., control signal application 320) stored or included on a computer readable medium, such as the memory 310 of the vehicle control unit 70 described above, for example.

According to the method 400, at a block 410, the thermal harvesting device 20 generates electricity based on a temperature differential to power the battery 30 or a capacitor. At a block 420, the battery 30 or a capacitor powers the sensor 40 and the wireless transmitter 60. At a block 430, the sensor 40 measures data reflecting a parameter of the vehicle system 50 that creates a temperature differential (or another vehicle system 50). At a block 440, the sensor 40 outputs a signal representing the measured data to the wireless transmitter 60 and the wireless transmitter 60 transmits the signal to the computing unit 70.

Various embodiments of the present disclosure are disclosed herein. The disclosed embodiments are merely examples that may be embodied in various and alternative forms, and combinations thereof. As used herein, for example, "exemplary," and similar terms, refer expansively to embodiments that serve as an illustration, specimen, model or pattern.

The above-described embodiments are merely exemplary illustrations of implementations set forth for a clear understanding of the principles of the disclosure. Variations, modifications, and combinations may be made to the above-described embodiments without departing from the scope of the claims. All such variations, modifications, and combinations are included herein by the scope of this disclosure and the following claims.

What is claimed is:

1. A vehicle measurement system, comprising:
a thermoelectric module connected to a vehicle exhaust system and configured to generate electricity based on a temperature differential created by the vehicle exhaust system;
a sensor configured to measure a characteristic reflecting a parameter of a fuel storage system and output a signal, and to receive power from the thermoelectric module connected to the vehicle exhaust system; and
a wireless transmitter in communication with the sensor and configured to:
receive power from the thermoelectric module;
receive the signal from the sensor; and
transmit the signal that is received from the sensor;
wherein the thermoelectric module is configured and arranged to power the sensor and the wireless transmitter.

2. The vehicle measurement system of claim 1, wherein:
the sensor is a first sensor, the parameter is a first parameter, and the signal is a first signal;
the vehicle measurement system comprises a second sensor configured to measure a characteristic reflecting a second parameter of the fuel storage system and output a second signal; and
the wireless transmitter is configured to receive the second signal from the second sensor and transmit the second signal that is received from the second sensor; and
the thermoelectric module is configured to power the second sensor.

3. The vehicle measurement system of claim 1, further comprising a battery that is charged by the thermoelectric module, wherein the battery is configured to power at least one of the sensor and the wireless transmitter.

4. The vehicle measurement system of claim 3, wherein the battery is configured to power each of the sensor and the wireless transmitter.

5. The vehicle measurement system of claim 1, wherein the temperature differential is between a first temperature closer to the vehicle exhaust system and a second temperature farther away from the vehicle exhaust system.

6. The vehicle measurement system of claim 1, further comprising a vehicle control unit, wherein the wireless transmitter is configured to be wirelessly coupled to the vehicle control unit.

7. The vehicle measurement system of claim 6, wherein the vehicle control unit is one of an engine control module and a body control module.

8. The vehicle measurement system of claim 1, wherein the parameter is one of fuel level, liquid pressure, vapor pressure, and ethanol.

9. The vehicle measurement system of claim 1, wherein:
the sensor is a first sensor, the parameter is a first parameter, and the signal is a first signal;
the vehicle measurement system comprises a second sensor configured to measure a characteristic reflecting a second parameter of the fuel storage system and output a second signal; and
the wireless transmitter is configured to receive the second signal from the second sensor and transmit the second signal that is received from the second sensor.

10. The vehicle measurement system of claim 9, wherein the thermoelectric module is configured to power the second sensor the sensor and the wireless transmitter.

11. A vehicle measurement system, comprising:
a thermoelectric module connected to a first vehicle system and configured to generate electricity based on a temperature differential, and to receive power from the thermoelectric module connected to the vehicle exhaust system;
a sensor configured to measure a characteristic reflecting a parameter of a second vehicle system and output a signal, and to receive power from the thermoelectric module connected to the vehicle exhaust system;
a wireless transmitter in communication with the sensor and configured to:
receive power from the thermoelectric module;
receive the signal from the sensor; and
transmit the signal that is received from the sensor; and
a vehicle control unit, wherein the wireless transmitter is configured to be wirelessly coupled to the vehicle control unit;
wherein the thermoelectric module is configured and arranged to power the sensor and the wireless transmitter.

12. The vehicle measurement system of claim 11, wherein:
the sensor is a first sensor, the parameter is a first parameter, and the signal is a first signal;
the vehicle measurement system comprises a second sensor configured to measure a characteristic reflecting a second parameter of the fuel storage system and output a second signal; and the wireless transmitter is configured to receive the second signal from the second sensor and transmit the second signal that is received from the second sensor; and the thermoelectric module is configured to power the second sensor.

13. The vehicle measurement system of claim 11, further comprising a battery that is charged by the thermoelectric module, wherein the battery is configured to power at least one of the sensor and the wireless transmitter.

14. The vehicle measurement system of claim 13, wherein the battery is configured to power each of the sensor and the wireless transmitter.

15. The vehicle measurement system of claim 11, wherein the temperature differential is between a first temperature closer to the first vehicle system and a second temperature farther away from the first vehicle system.

16. The vehicle measurement system of claim 11, further comprising a vehicle control unit, wherein the wireless transmitter is configured to be wirelessly coupled to the vehicle control unit.

17. The vehicle measurement system of claim 16, wherein the vehicle control unit is configured to, based on a signal received from the wireless transmitter, generate a control signal for a third vehicle system.

18. The vehicle measurement system of claim 11, wherein:
the sensor is a first sensor, the parameter is a first parameter, and the signal is a first signal; and
the vehicle measurement system comprises at least a second sensor that is configured to measure a characteristic reflecting a second parameter and output a second signal.

19. The vehicle measurement system of claim 18, wherein the wireless transmitter is configured to: receive a second signal from the second sensor and transmit a second signal that is received from the second sensor.

20. The vehicle measurement system of claim 19, wherein the vehicle control unit is a first vehicle control unit and the wireless transmitter is configured to be wirelessly coupled to a second vehicle control unit.

21. A vehicle, comprising:
a plurality of vehicle systems;
a thermoelectric module connected to a first one of the plurality of vehicle systems and configured to generate electricity based on a temperature differential;
a sensor configured to measure a characteristic reflecting a parameter of one of the plurality of vehicle systems and output a signal and to receive power from the thermoelectric module connected to the vehicle exhaust system;
a wireless transmitter in communication with the sensor and configured to:
  receiver power from the thermoelectric module;
  receive the signal from the sensor; and
  transmit the signal that is received from the sensor; and
a vehicle control unit that is configured to control at least one of the plurality of vehicle systems, wherein the wireless transmitter is configured to be wirelessly coupled to the vehicle control unit;
wherein the thermoelectric module is configured to power the sensor and the wireless transmitter.

* * * * *